United States Patent [19]

Erickson

[11] Patent Number: 5,339,289
[45] Date of Patent: Aug. 16, 1994

[54] ACOUSTIC AND ULTRASOUND SENSOR WITH OPTICAL AMPLIFICATION

[76] Inventor: Jon W. Erickson, 3406 Rambow Dr., Palo Alto, Calif. 94306

[*] Notice: The portion of the term of this patent subsequent to Sep. 28, 2010, has been disclaimed.

[21] Appl. No.: 42,726

[22] Filed: Apr. 5, 1993

Related U.S. Application Data

[63] Continuation-in-part of Ser. No. 895,544, Jun. 8, 1992, Pat. No. 5,249,163.

[51] Int. Cl.$^5$ .............................................. G01H 1/00
[52] U.S. Cl. ..................................... 367/149; 367/151; 73/653; 73/655; 359/212; 359/214
[58] Field of Search ................ 367/149, 151; 73/653, 73/655; 359/212, 214

[56] References Cited

U.S. PATENT DOCUMENTS

| | | | |
|---|---|---|---|
| 3,708,231 | 1/1973 | Walters | 356/152 |
| 4,422,167 | 12/1983 | Shajenko | 367/149 |
| 4,446,543 | 5/1984 | McLandrich et al. | 367/149 |
| 4,998,225 | 3/1991 | Shajenko | 367/140 |

FOREIGN PATENT DOCUMENTS

| | | | |
|---|---|---|---|
| 3607868 | 9/1987 | Fed. Rep. of Germany | G01H 9/00 |

OTHER PUBLICATIONS

"Mesures optiques de déplacements . . ." 2001a Revue de Physique Appliquee 24 (1989) Aout, No. 8, Paris, FR.

"Opto-electronic system . . ." 8127 Review of Scientific Instruments 58 (1987) Sep., No. 8, New York, N.Y., USA.

*Primary Examiner*—J. Woodrow Eldred
*Attorney, Agent, or Firm*—James J. Leary

[57] ABSTRACT

An optical lever acoustic and ultrasound sensor with increased sensitivity using an optical amplification means to amplify the motion of an incident acoustic wave and convert it to an electric signal for image processing. Three approaches to the optical amplification are disclosed. In the first approach, the vibrating mirror is part of a cantilever that increases the angular deflection of the incident light beam. In the second approach, a second, stationary mirror is positioned approximately parallel to the vibrating mirror surface. The reflected light beam is reflected back onto the vibrating mirror, and picks up a another increment of the acoustic signal with each reflection. In the third approach, the effective moment of the optical lever is increased within a small volume by the use of two stationary mirrors to increase the path length from the vibrating mirror to the position-sensitive detector. This increases the relative movement of the light beam on the surface of the position-sensitive detector and, therefore, the overall sensitivity of the sensor. The incident beam of light is focused by a lens between the light source and the vibrating mirror, so that the focal point is in the plane of the position-sensitive detector. The smaller spot size and greater intensity of the incident light allows greater detector sensitivity. Two or more chopped light beams may be directed at a single vibrating surface, and phase-locked loop circuitry used to reduce the signal-to-noise ratio.

7 Claims, 5 Drawing Sheets

ACOUSTIC AND ULTRASOUND SENSOR WITH OPTICAL AMPLIFICATION

RELATIONSHIP TO OTHER APPLICATIONS

This patent application is a continuation-in-part of the co-pending patent application of Jon W. Erickson, Ser. No. 07/895,544, filed June 8,1992, now Pat. No. 5,249,163 for an Optical Lever for Acoustic and Ultrasound Sensor, the specification of which is hereby incorporated by reference in its entirety.

FIELD OF THE INVENTION

The present invention relates generally to diagnostic medical instrumentation and, more particularly, to ultrasonic transducers used in medical imaging. A primary objective of the present invention is to provide a robust, low-cost compact transducer with greatly increased sensitivity to ultrasound signals.

BACKGROUND OF THE INVENTION

A typical ultrasonic imaging system makes use of one or more piezoelectric transducers which act as the source (actuator) of the ultrasonic beam or signal, and which often also serve to sense the reflected signal (sensor). An electrical pulse generated by an electronic control module is converted to an ultrasonic pulse by the transducer/actuator in the probe. The probe is in contact with the body, and the ultrasonic pulse is transmitted through the probe into the body. The pulse is then absorbed by body tissues or reflected to different degrees from the boundaries between body tissues. The reflections reach the transducer/sensor at different times, which vary with distance to the tissue boundaries. The reflections also have different energies, due to the different acoustic impedances of the tissues, as well as absorption by the intervening tissues. The transducer/sensor converts the reflections into a weak electrical signal, which contains information that can be processed into an image of the body.

A great variety if ultrasonic transducers are presently in use or under development. Shapes and sizes vary widely in order to meet special needs. Focusing by electronic or mechanical means, or some combination thereof, can be used to produce and steer a narrow ultrasonic beam of desired focal length. Likewise, mechanical and electronic focusing can be used to sense the reflections from a particular direction and distance. Phased transducer arrays of various configurations have been employed to achieve particular focusing properties, under electronic control.r63he term "phased array" is taken from radar technology, in which the phase relationships of signals from multiple antennae are processed electronically to improve resolution and sensitivity.) The acquired signal is then converted into an image using analog or, depending on cost and technological considerations, digital processing.

Good resolution of ultrasound images is important for medical applications. Some limits to resolution are fundamental to the physics of wave propagation (for example, acoustic shadows and reverberations, and geometric artifacts) and are best dealt with by educating the user, or by appropriate image processing algorithms. Other factors affecting resolution involve transducers and electronic instrumentation (such as axial and lateral resolution, and dynamic range) and are susceptible to improvement.

Axial resolution can be limited in part by wavelength of the ultrasonic signal ("ultrasound" simply designates sound waves of a frequency above the audible range, with wavelengths of millimeters or less). Absorption of ultrasonic energy by body tissues tends to restrict the useful depth of field to about 200 wavelengths, due to attenuation of the signal. Thus resolution can be improved by use of shorter wavelengths (higher frequencies) but this implies a shallower depth of field.

For a simple system with a single element and spherical or parabolic focusing, the lateral resolution is limited by the aperture of the transducer. Larger apertures provide greater resolution but shallower depth of field. The size of the transducer element or elements also can limit the resolution, since the detected signal will be known to originate from a given transducer but not any particular location on that transducer.

The dynamic range of the instrument determines the useful number of gray scale levels in the image. Most commercial transducer use piezoelectric crystal elements or other materials (e.g. piezoelectric polymers such as polyvinylidenefluoride) both as actuators which produce the ultrasonic pulse, and as sensors which detect the reflected signal. The physics and engineering of piezoelectric sensors are relatively well understood. The sensitivity of a simple piezoelectric sensor, such as a small block of quartz, can be greatly improved by use of a more complicated geometry, the "piezoelectric bimorph" shape. The bimorph has been used since 1930 in microphones and phonograph needle assemblies, but various design considerations such as high cost and fragility preclude its use in ultrasound transducers.

An alternative means of sensing small deflections or increments of motion is the optical lever. Optical levers have proven to be effective in routine measurements of extremely small deflections, of less than 0.01 nanometer, in atomic force microscopy (AFM). This measurement strategy can be implemented in robust ultrasound transducers at low cost, with great flexibility in design.

In the inventor's previous patent application, an acoustic sensor is presented which uses an optical lever to amplify ultrasonic signals. The signal amplification provided by the sensor is dependent on the geometry of the optical lever. Even though the optical lever arrangement presented is capable of very high signal amplification, there are practical limitations to the level of amplification possible before the size of the sensor becomes unwieldy. The present invention seeks to overcome these limitations by presenting an optical lever acoustic sensor which uses an optical amplification means to amplify acoustic or ultrasonic signals to an even greater degree without significantly increasing the size of the sensor.

SUMMARY OF THE INVENTION

The objective of the present invention is to provide an optical lever acoustic and ultrasound sensor with increased sensitivity to acoustic signals. It is an important part of this objective to provide the desired increase in sensitivity by an optical amplification means which amplifies the motion of an incident acoustic wave and converts it to an electrical signal for image processing. An optical amplification means is preferred because it is not subject to the same signal-to-noise limitations as the electronic amplifiers typically used in the prior art. The optical amplification means is also capable of operating in harsh environments with high levels of electromagnetic interference that would render prior art electronic amplifiers ineffective, since they amplify the electronic noise as well as the signal.

It is also an objective of the invention to provide a compact acoustic sensor where the optical amplification means does not significantly increase the overall size of the sensor. At the same time, it is an objective to provide a highly sensitive acoustic sensor that is both robust and low cost to manufacture.

In distinct contrast to the piezoelectric transducer/sensors of the prior art, the present invention uses an optical lever to detect acoustic signals, such as ultrasonic waves. The original optical lever acoustic sensor makes use of a beam of light shining on a mirrored surface M1 (e.g. a cantilever, membrane, or piston) in good acoustic contact with the ultrasonic medium. The surface M1 changes angle in response to acoustic excitation. The reflected beam of light is finally directed onto a position-sensitive detector. Small movements in the mirrored surface M1 result in relatively large changes in the position where the beam of light strikes the detector.

The present invention proposes several improvements to the basic design of the optical lever acoustic sensor which include an optical amplification means for improving the sensitivity of the sensor. Three different approaches to the optical amplification are the disclosed which can be used separately or in combination with one another.

In the first approach to optical amplification, the vibrating mirror M1 is made part of a cantilever arrangement that increases the angular deflection of the incident light beam. The acoustic energy impinging on the large area of the diaphragm is transferred into the small area of the post. The post is connected to the cantilevered mirror M1 at a point close to the hinge, in order to increase the angular deflection for a given increment of vertical deflection, and hence the overall sensitivity.

In the second approach to optical amplification, a second, stationary mirror M2 is positioned approximately parallel to the vibrating mirror surface. The reflected beam of light is directed by the stationary mirror M2 back onto the vibrating mirror M1, and picks up a second increment of information about the acoustic signal with each increment in angular deflection. Even more reflections may be included so as to increase the total number of signal increments, the total signal in the light beam being proportional to the number of times the light beam has been reflected from the vibrating surface M1.

In the third approach to optical amplification, the effective moment of the optical lever is increased within a small volume by the use of additional stationary mirrors M3 and M4. The stationary mirrors are introduced to increase the length of the path which the reflected beam of light must follow before arriving at the position-sensitive detector. This increases the relative movement of the light beam on the surface of the position-sensitive detector and, therefore, the overall sensitivity of the sensor.

Furthermore, the following improvements are made to the sensor so that it can take fuller advantage of optical amplification methods just described. The incident beam of light is focused by a lens between the light source and the vibrating mirror M1, so that the focal point is in the plane of the position-sensitive detector. The smaller spot size and greater intensity of the incident light offers the potential for greater detector sensitivity.

Under some conditions, it may be desirable to direct two or more beams of light at a single vibrating surface M1. One example is when the light beams are chopped so phase-locked loops can reduce the signal bandwith, and increase the signal-to-noise ratio. Two or more frequencies may be sampled simultaneously by directing two or more independently chopped light beams onto a single surface M1. Electronic cross-talk may be minimized by the use of a separate position-sensitive detector for each beam.

Small movements in the mirrored surface M1 result in relatively large changes in the position where the beam of light strikes the detector. The position-sensitive detector is insensitive to fluctuations in the light intensity, which lowers the overall costs (especially in arrays of such sensors). The size of the sensor and of the transducer as a whole can also be reduced considerably, since all the components can be fabricated with microelectronic techniques. Other objects and advantages of the invention will no doubt occur to those skilled in the art upon reading and understanding the following detailed description along with the accompanying drawings.

DESCRIPTION OF THE PREFERRED EMBODIMENTS

Figure 1:
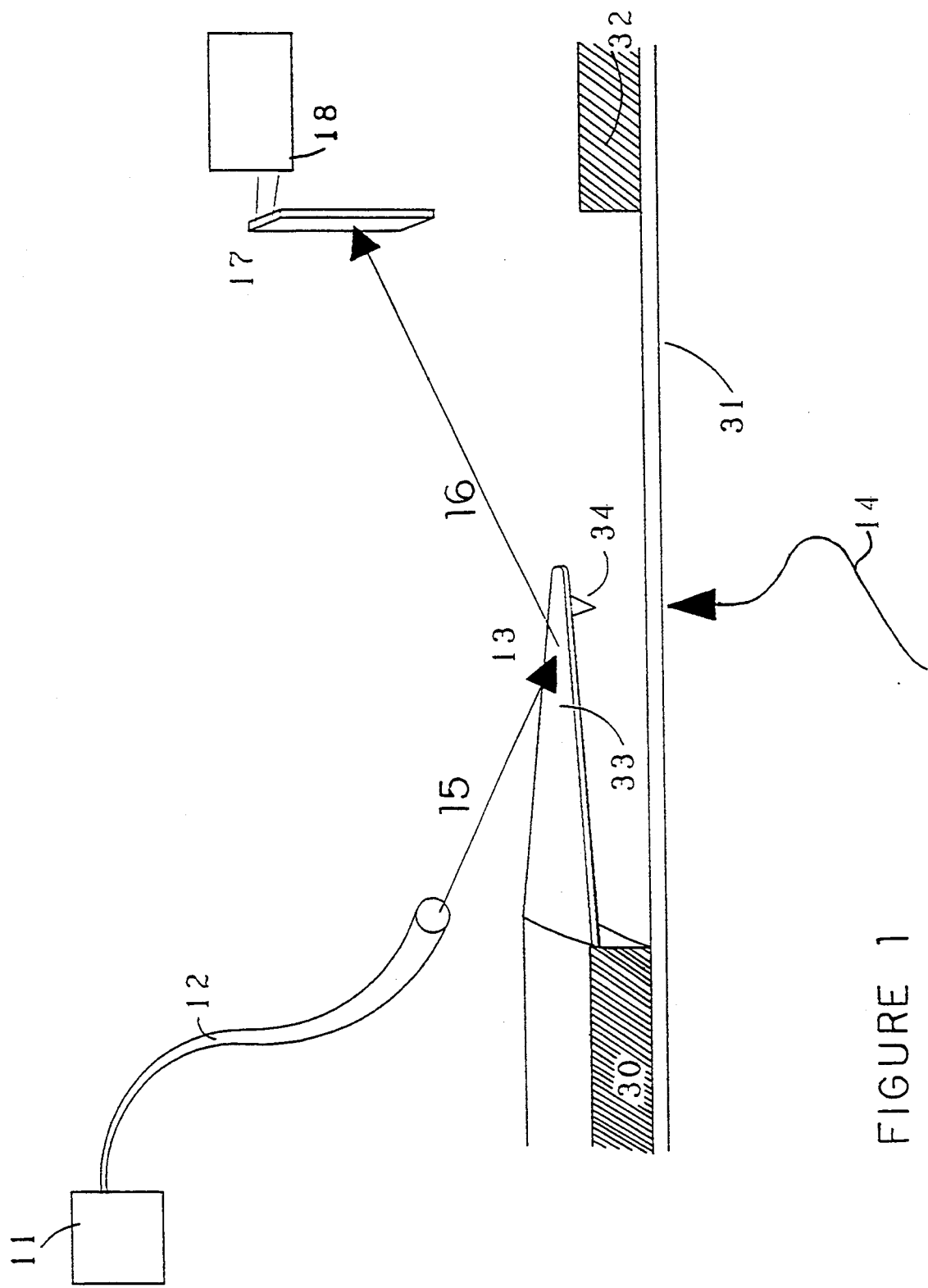
FIG. 1 shows a schematic view of the original optical lever ultrasound sensor.

FIG. 1 shows a schematic view of an optical lever ultrasound sensor built in accordance with the inventor's previous patent application. A light source 11 is used to generate a narrow beam of collimated light 15 which is directed toward a reflective surface 13 at an acute angle to the surface. In the preferred embodiment, the light source 11 is a laser light source and a single mode optical fiber 12 directs the beam of light 15 onto the reflective surface 13. Alternatively, a source of collimated light other than a laser may be coupled to the optical fiber 12, or a laser light source, for instance an integrated AlGaAs/GaAs diode laser, may be used to direct a beam of light 15 directly onto the reflective surface 13 without the use of an optical fiber 12.

In this illustrative embodiment, a cantilever 33 is mounted on a substrate 30 having a membrane 31 formed across an acoustic aperture 32. The cantilever 33 contacts the membrane 31 near the middle of the aperture 32 by means of a stylus 34 or other coupling link. A reflective surface 13 is formed on the back of the cantilever 33. The reflective surface 13 is thus coupled to the membrane 10 which moves in reaction to an incident ultrasonic wave 14. The incident light beam strikes the moving reflective surface. The reflected light beam 16 from the reflective surface 13 strikes a position-sensitive light detector (PSD) 17, which generates a signal indicative of the position at which the beam of light 16 strikes the PSD 17. When the membrane 31 is at rest, the reflected light beam 16 strikes somewhere near the center of the PSD 17. The small movements of the reflective surface 13 due to the incoming ultrasonic wave 14, result in large movements of the position at which the reflected light 16 strikes the PSD 17. The PSD 17 is sensitive to movements of greater than 5 nm in the location of the spot of light on it. The deflection of the reflective surface 13 is thus amplified by this optical lever, the amplification being determined by the angular displacement of the reflective surface for a given level of acoustic pressure and the length of the "lever arm", which is the distance of the PSD 17 from the reflective sensor surface 13.

The output of the PSD 17 is a voltage signal which varies in proportion to the position of the light spot on the PSD surface, which in turn is proportional to the amplitude of the vibrations of the reflective sensor surface 13, and to the amplitude of the ultrasonic pressure wave 14. The signal has a very low level of noise due to the measurement process or strategy. Alternatively, a position sensitive detector whose output is a digital signal indicative of the position of the light spot on the PSD surface can be used.

The PSD 17 output is processed by the imaging electronics 18, either as a single element or as one channel of an array of sensors. The leading edge of the incident pulse may be used in such an array to electronically focus on the position of the echo source. This positional information is then used to build up an image of the objects or tissue interfaces responsible for the echoes.

The present invention works analogously to the inventor's previous invention just described and at the same time improves upon it by providing even greater amplification of the acoustic signal. To accomplish this, the amplification of the sensor can be increased by optical means which effectively increase the angular displacement of the reflective surface for a given level of acoustic pressure or which increase the length of the "lever arm" of the optical lever.

Figure 2:
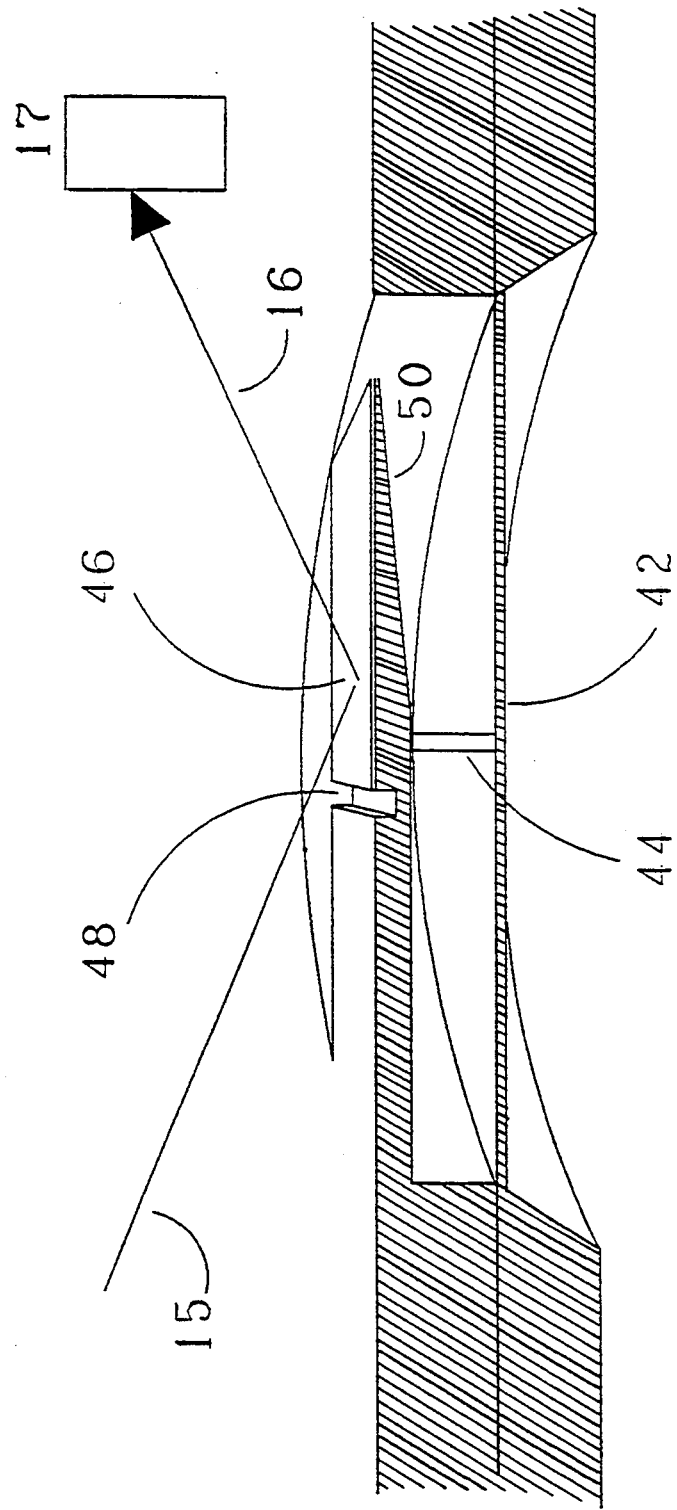
FIG. 2 shows a cutaway view of an ultrasound sensor element having a cantilevered light reflective surface which gives additional sensitivity by increasing the angular deflection for a given increment of acoustic pressure.

FIG. 2 illustrates the present invention using a first approach to optical amplification of the acoustic signal. This approach uses an arrangement of the cantilever which offers move sensitivity at relatively little cost. In analogy to the leverage provided by the malleus and stapes of the human ear, this mechanical arrangement concentrates the acoustic energy impinging on the large membrane 42 into the smaller area of the post 44. The top of the post 44 pushes up the cantilevered mirror 46 at a location close to its hinge 48. This forms a class three lever which maximizes the angular deflection of the reflective surface for a given amplitude of movement in the membrane. The increased angular deflection of the reflective surface results in greater relative movement of the reflected light beam on the PSD which increases the overall amplification of the sensor. The design is compatible with contemporary silicon/-silicon dioxide micromachine technology, and permits impedance matching at particular frequency ranges of interest.

In this design, the acoustic impedance of the sensor is determined by the combined mass of the cantilever and the membrane, and the combined stiffness of the cantilever 50 and the membrane 42. This allows additional flexibility in the design of the sensor for matching impedance and for tuning the sensitivity of the sensor. The cantilever can also be used to linearize the pressure response of the sensor. If the response of the membrane sensor by itself does not obey Hooke's law, a cantilever with the desired force constant may be added to improve the sensor's linearity.

Figure 3:
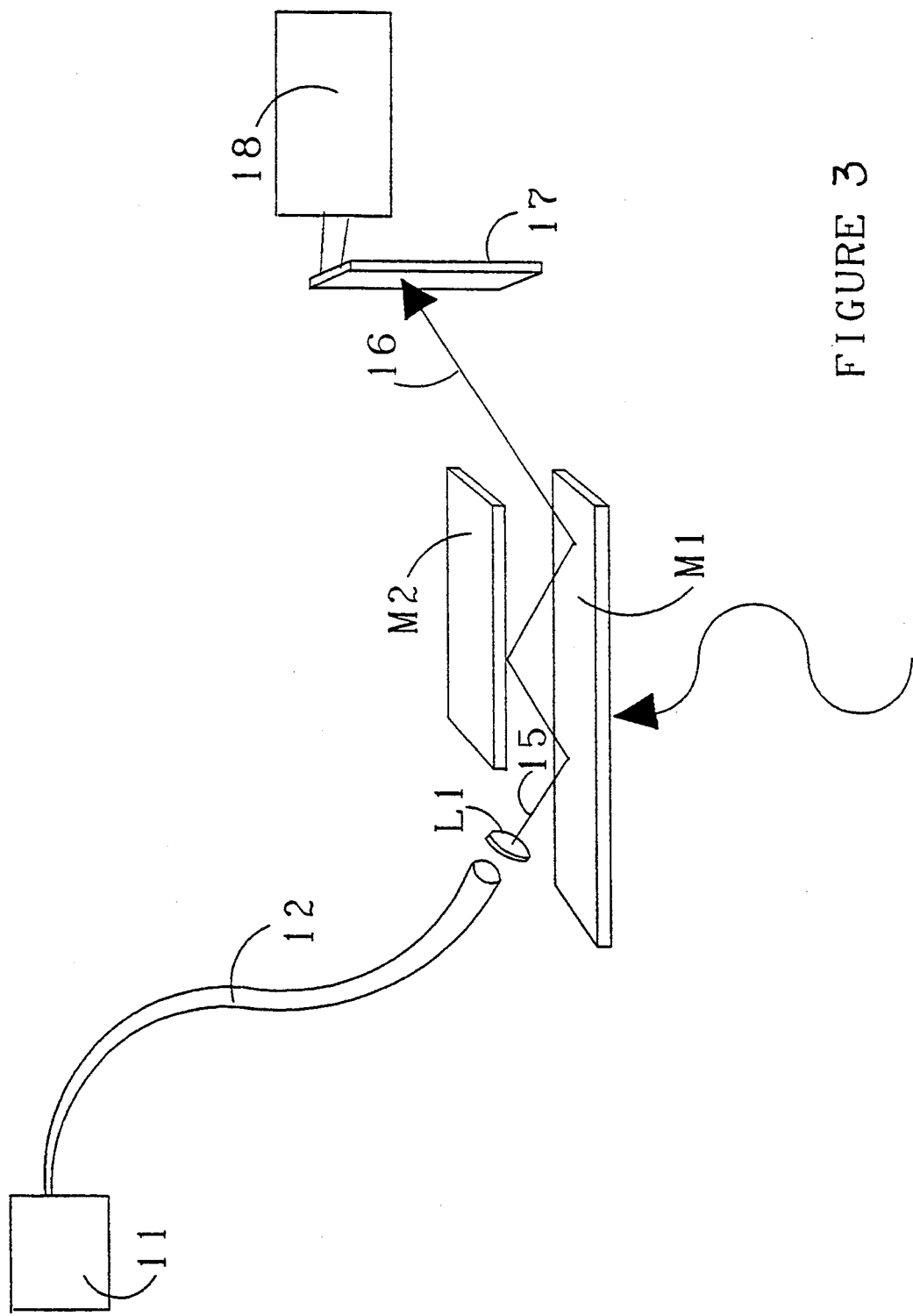
FIG. 3 shows a multiple-bounce arrangement in which the light beam is redirected onto the vibrating mirror surface M1 by a second, stationary mirror M2.

FIG. 3 shows an embodiment of the present invention which uses a multiple bounce approach to optical amplification of the acoustic signal. The light beam (focused onto the detector by lens L1) strikes the vibrating mirror surface M1, and then is reflected onto a stationary mirror M2. The light beam is reflected from M2 back onto the vibrating surface M1 again. Each reflection from M1 adds an increment of signal to the light beam, in the form of angular deflection, so that after two such reflection or bounces the amplitude of the angular signal is doubled. With high-reflectivity mirrors, many such bounces can be achieved with relatively little loss of light intensity. The greater angular deflection of the incident light beam for a given amplitude of movement of the vibrating mirror surface M1 results in greater relative movement of the reflected light beam 16 on the PSD 17 which increases the overall amplification of the sensor.

The PSD 17 is only sensitive to the position of the light beam, not the intensity, so some loss in the intensity of the light beam due to the multiple reflections can be tolerated without affecting the overall sensitivity of the acoustic sensor. The mirrors may be metal films (such as Cr, Cu, Ag, or Au) which can achieve reflectivities of about 99.4%. After 100 bounces with 99.4% reflectivity the light beam intensity would be 54.78% of the original value, which is quite acceptable. If greater numbers of bounces are required to achieve the desired amplification, multilayer films (such as of alternating Si and $SiO_2$ layers with quarter-wavelength matching) may be used to increase the reflectivity to about 99.93%. After 1000 bounces with 99.4% reflectivity the light beam intensity is reduced to about 0.24% of the original value, while with 99.93% reflectivity it retains approximately 49.6% of the original value. Moreover, scattering and absorption are reduced by using multilayer films.

Figure 4:
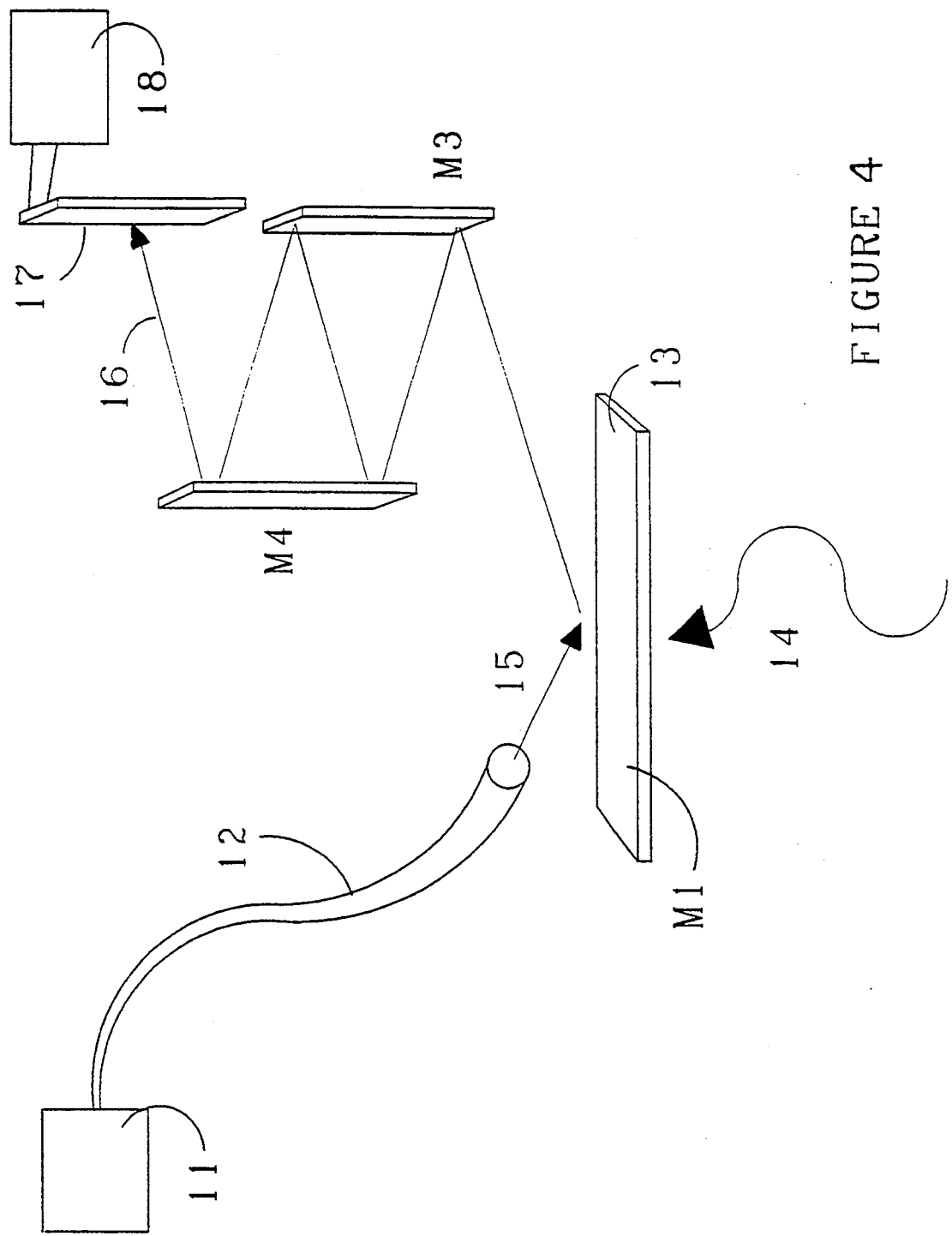
FIG. 4 shows the use of two additional stationary mirrors M3 and M4 to "fold" a long lever arm into a more compact volume.

FIG. 4 illustrates the third approach to optical amplification of the acoustic signal by increasing the "lever arm" of the optical lever. As mentioned previously, the amplification of the sensor is partially determined by the length of the "lever arm", which is the distance of the PSD 17 from the reflective sensor surface 13. If sensor size were of no concern, the sensitivity of the acoustic sensor could be increased by simply making this distance larger. In practice, however, this approach would eventually make the overall size of the sensor very unwieldy. In order to overcome the problem of size, this embodiment of the invention provides two stationary mirrors M3 and M4 which are used to "fold" a long lever arm into a more compact volume. Doubling the path length the reflected light beam travels between the reflective sensor surface 13 and the PSD 17 doubles the relative movement of the light beam on the PSD, thereby doubling the amplification provided by the optical lever. As in the previous embodiment, with highly reflective mirrors the amplification of the sensor can be increased tremendously by multiple reflections of the light beam to increase the length of the lever arm.

Figure 5:
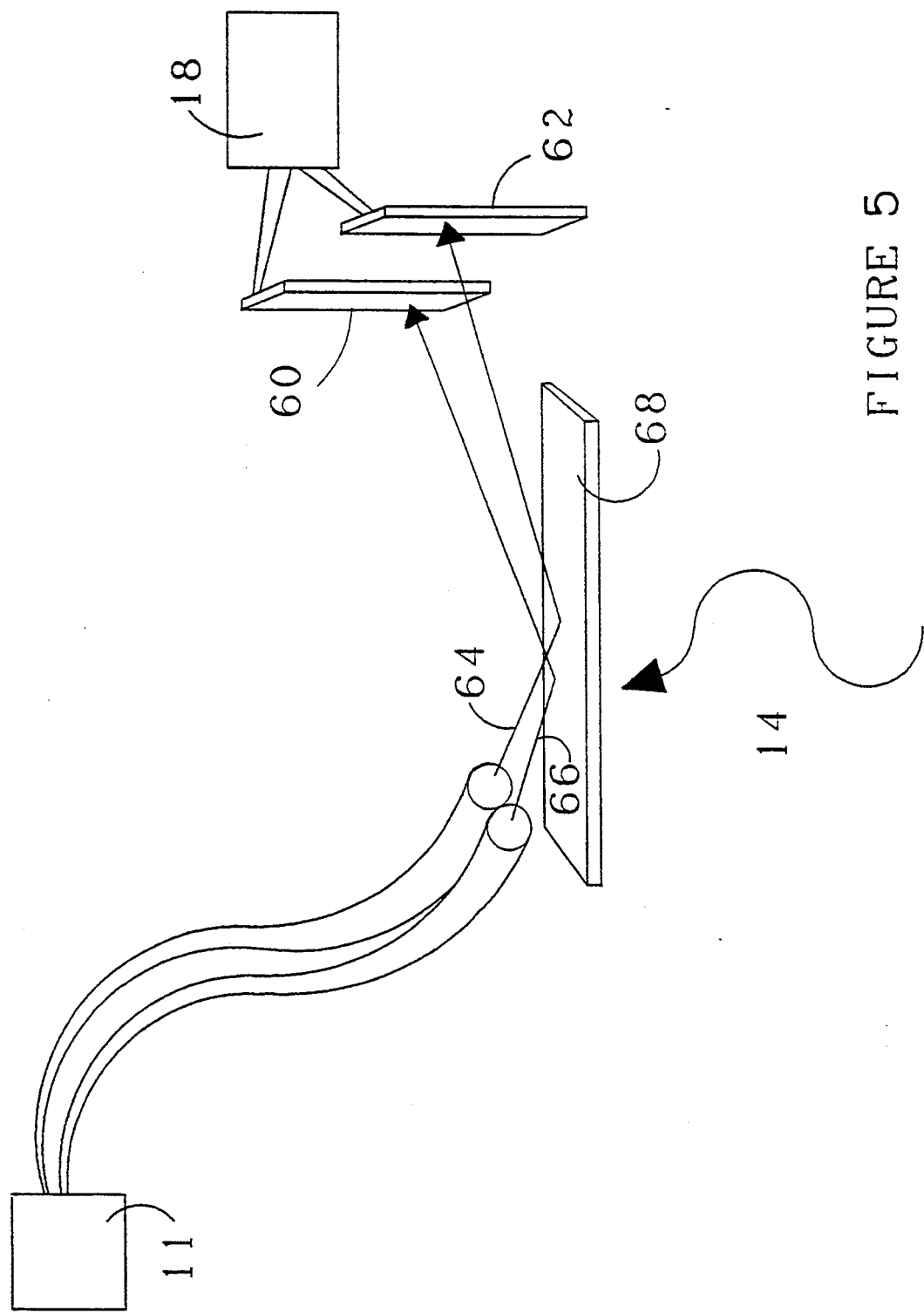
FIG. 5 shows two independent light beams striking a single vibrating surface, and being detected by two independent position-sensitive detectors.

FIG. 5 shows two independent light beams 64,66 striking a single vibrating surface 68, and being detected by two independent position-sensitive sensitive detectors 60,62. This illustrates the use of multiple independent phase-locked loops, each chopping a light beam at a unique frequency, to measure a given frequency component of the acoustic excitation. The signal-to-noise ratio can be improved significantly by decreasing the bandwidth of the detection circuitry. The comparison of two (or more) measurements at different frequencies can be used to eliminate certain kinds of artifacts in ultrasonic images. Finally, two (or more) detection frequencies are of great utility in the Doppler or color Doppler modes of medical ultrasonic imaging. Implementation of separate phase-locked loops in the sensor hardware may better achieve the optimal results, of narrow bandwidths at multiple frequencies.

It is worth noting that, while FIG. 5 shows how multiple light beams can be directed at different azimuthal angles onto a vibrating mirror, it is also possible to use multiple light beams of different wavelengths on a vibrating grating to achieve an analogous result in reciprocal space.

Technical Discussion

Sensitivity

A typical piezoelectric sensor may have a sensitivity, measured in units of power per area, on the order of $10^{-7}$ Watt cm$^{-2}$. When operating at a recommended biological threshold limit of about $10^{-2}$ Watt cm$^{-2}$, signal attenuation due to absorption by biological tissue limits the depth of view to about 200 wavelengths. For a 3 MHz signal, a 10 cm depth corresponds to a loss of about 5 orders of magnitude in signal strength.

In contrast, an optical lever sensor can detect signals of less than $10^{-18}$ W.cm$^{-2}$. (This corresponds to a routine situation in AFM involving a deflection of 0.01 nm against a force constant of 2 Newton m$^{-1}$, measured in less than $10^{-3}$ second.) Thus an initial signal of $10^{-2}$ Watt cm$^{-2}$ will in theory still be detectable even after it has been attenuated by 16 orders of magnitude. With the additional improvements to the optical lever acoustic sensor described above, the practical limits of sensor sensitivity can be pushed even closer to the theoretical limit, in cost effective ways.

The increased sensitivity (with respect to conventional piezoelectric transducers) can be used in several different ways. The size of the sensor may be reduced, which may have advantages in terms of image resolution (both axial and lateral). The dynamic range of the acquired signal may be increased, which can be used to improve image quality. The power of the initial signal may be decreased, which may be a consideration for examination of certain kinds of biological tissue (e.g. eyes, embryos). Shorter wavelengths of ultrasound may be used while still viewing depths of at least 10 cm, which would improve axial resolution.

Dynamic Range

In practice, it is convenient to limit the dynamic range to 12 orders of magnitude or less. The practical constraints on dynamic range are the amplitude of the deflection produced by the ultrasound excitation of the membrane, diaphragm, or piston; and the size of the position-sensitive detector (PSD). A nearly linear response of the vibrating surface to the excitation is desirable, and this will constrain the acceptable amplitude.

Should larger amplitudes be acceptable for the vibrating surface in a given implementation, it may be useful to adjust the sensitivity. Range switching is accomplished relatively easily, by shortening the lever arm, or moving the PSD closer to the point of reflection. A typical commercially available PSD is about 5 mm in length and can distinguish positions of incident light that are separated by more than about 5 nm. This gives a dynamic range of about 6 orders of magnitude in amplitude, or about 12 orders of magnitude in intensity. If the distance to the point of reflection is shortened by a factor of 100, the sensitivity will be less, but signals 100 times larger in amplitude (or 10,000 in intensity) may be measured.

The improvements may permit better or more convenient utilization of the dynamic range. For example, the mirrors M3 and M4 in FIG. 4 may be adjusted to alter the lever arm. The number of bounces involving mirror M2 in FIG. 3 may be altered by changing the incident angle of the light beam, or the position of mirror M2 relative to the vibrating mirror M1.

Resolution

When a sensor is smaller in size than the wavelength of the detected signal, the phase of the signal becomes an important parameter in determining the resolution. Pulsewidth or the duration of the excitation may be of less concern. For example, the small size and great sensitivity of the sensor can be used to detect the phase of the wave and identify the leading edge, rather than the entire pulse. If the arriving edge detection is very efficient, the axial resolution may be limited only by the lateral solid angle subtended by the sensor.

Lateral resolution also may be enhanced by the small size of the sensor. Most present designs do not detect where on a given sensor element the incident ultrasound wave impinges. Therefore, the lateral resolution is limited not only by the distance between sensor elements, but by the size of each element.

Thermal and Other Noise

Thermal and other energy fluctuations will provide a background of vibrations in the ultrasound frequency range, for which the probability can be readily estimated. Well known techniques exist for addressing this problem, such as moving the signal to a part of the frequency domain which is lower in noise, or the use of a lock-in amplifier.

The use of multiple beams, phase-locked loops, independent chopping and detection can reduce the sensitivity of the system to such thermal fluctuations. Comparison of signals obtained at two or more frequencies can be used to reduce artifacts in images acquired by ultrasound. Separate phase-locked loops may be optimized in hardware, to give better results in Doppler or color Doppler ultrasound imaging.

Linear and Square Arrays

This measurement strategy lends itself to high-yield, low-cost manufacture. In most implementations a separate actuator and sensor is required, instead of the single transducer. However, the low cost should compensate for the separation of functions. Moreover, the separation of functions itself should permit the use of cheaper materials that need not serve both as actuator and sensor.

The sensor elements can be scaled over a wide range of sizes. Arrays of such elements can be used in electronic focusing. Generally linear arrays have proved adequate in medical imaging, since two dimensions suffice for most present diagnostic purposes. Square or two-dimensional arrays are also possible, giving rise to the possibility of three-dimensional ultrasonic imaging.

It should be noted that the various improvements such as the reconfigured cantilever, the multiple-bounce design, or the use of two or more incident beams on a single vibrating surface, can be incorporated into arrays.

The Reflective Surface

The reflective surface must be in good acoustic contact with the ultrasonic medium, and should be displaced similarly by waves of similar amplitude. The simplest response function is linear. For example, the surface response will obey Hooke's law ($F=kx$) if the force opposing displacement is proportional to the magnitude of the displacement. The displacement due to the incident ultrasonic wave or pulse must also be quickly damped, in order to avoid subsequent ringing or spurious signal.

A stable force constant can be achieved in various implementations. Examples include silicon or polymer membranes or diaphragms, solid or fluid pistons, and micromachined springs or cantilevers.

Membranes or diaphragms designate thin, usually circular and planar bodies fastened at the periphery to a thicker support. Often the material itself opposes motion out of the plane of the resting surface, although another force constant may be imposed (e.g. the cantilever in FIG. 2). An air-fluid interface by itself provides a simple reflective surface in which surface tension opposes displacement, but also presents many design problems incompatible with a wide variety of sensor applications. Membranes and diaphragms made of solids such as silicon, or polymers of various kinds, are, however, the preferred choice in most applications.

Pistons designate either solids or fluids (liquids or gases) which move along the axis of a cylindrical cavity in response to the ultrasonic wave. Problems of friction would seem to be more readily overcome with fluid pistons, such as ferromagnetic liquids. The movement of the piston is typically opposed by a force proportional to the displacement, for example due to compression of a solid spring or a volume of gas.

The above examples serve simply to illustrate ways to design or fabricate a reflective surface with a reproducible and sensitive response to ultrasonic excitation.

Conclusion, Ramifications, and Scope

The improvements can be incorporated in various alternatives to the embodiments described above.

Both analog and digital signal processing can be used with virtually no changes from current imaging technology. This allows full use of the great art and ingenuity presently achieved in ultrasound signal processing, to deliver the maximum diagnostic value in medical care.

SENSITIVITY. Very low noise is integral to the design. The optical lever in effect acts as an amplifier with a high gain and low noise. The improvements can be incorporated in various alternatives to the embodiments described above.

RESOLUTION. High axial resolution is possible, perhaps even with longer wavelengths of ultrasound. Sensor elements smaller than the wavelength can be used, which should permit reliable measurement of phase.

Similarly small sensor elements can aid in improving lateral resolution, by increasing the precision with which the signal coordinates are determined.

ROBUST. Optical levers have already proven to be a robust measurement strategy.

LOW COST. The cost is low, and suitable for arrays and wide range of designs (e.g. catheter or invasive as well as non-invasive sensing). A single laser source can be used for an entire array of sensors, with a suitable number of optical fibers.

The ultrasound source or transducer/actuator can be made up of less expensive piezoelectric materials, since these do not need to play a dual role as transducer/sensors as well.

SUITED TO MINIATURIZATION AND MASS-PRODUCTION. The improvements involve design elements which are compatible with planar microfabrication technology, and which may be incorporated to further reduce the size of the sensor(s).

LOW-POWER. The sensor design requires only low power levels and thus is well-suited to use in portable ultrasound units. The great sensitivity of the sensor requires less power in the ultrasound source as well. The power needed to drive the ultrasound source or transducer/actuators can be reduced, due to the sensitivity of the transducer/sensors.

DYNAMIC RANGE. The greater sensitivity and lower noise of the design confer an increased dynamic range. This can be used to deliver better image clarity, with its attendant clinical diagnostic values.

OTHER APPLICATIONS. Though specifically conceived for use as an ultrasound transducer, the optical lever acoustic sensor of the present invention is also suitable for use as a microphone or hydrophone in the ultrasonic or audible range. With proper calibration, the present invention would also be useful as a pressure transducer for measurement of static or dynamic fluid pressure.

While the foregoing description contains many specific details, these should not be construed as limitations on the scope of the invention, but rather as an exemplification of some of its preferred embodiments. Many other variations are possible and will no doubt occur to others upon reading and understanding the preceding description. Accordingly, the scope of the invention should be determined, not by the embodiment illustrated, but by the appended claims and their legal equivalents.

I claim:

1. An acoustic sensor comprising:
   a first reflective surface responsive to incident sound waves,
   a light beam incident upon said reflective surface,
   a reflected light beam which is the reflection of said incident light beam from said first reflective surface,
   a position sensitive light detector so arranged as to sense the position of said reflected light beam,
   and optical means for amplifying a movement of said position of said reflected light beam on said position sensitive light detector in response to said incident sound waves.

2. The acoustic sensor of claim 1 wherein said optical means for amplifying comprises at least one stationary reflective surface, said reflected light beam being reflected at least once from said at least one stationary reflective surface before striking said position sensitive light detector.

3. The acoustic sensor of claim 2 wherein said at least one stationary reflective surface amplifies the movement of said position of said reflected light beam on said position sensitive light detector by increasing the path length travelled by said reflected light beam from said first reflective surface to said position sensitive light detector.

4. The acoustic sensor of claim 3 wherein said at least one stationary reflective surface comprises at least two stationary reflective surfaces, said reflected light beam being reflected at least once from each of said at least two stationary reflective surfaces before striking said position sensitive light detector.

5. The acoustic sensor of claim 4 wherein said reflected light beam is reflected multiple times from each of said at least two stationary reflective surfaces before striking said position sensitive light detector.

6. The acoustic sensor of claim 2 wherein said reflected light beam is reflected by said at least one stationary reflective surface back onto said first reflective surface at least once before striking said position sensitive light detector.

7. The acoustic sensor of claim 6 wherein said reflected light beam is reflected multiple times from said at least one stationary reflective surface back onto said first reflective surface before striking said position sensitive light detector.

* * * * *